US005199123A

United States Patent [19]
Jacques et al.

[11] Patent Number: 5,199,123
[45] Date of Patent: * Apr. 6, 1993

[54] EXAMINATION BED FOR NMR OR TOMODENSITOMETRY APPARATUS

[75] Inventors: Sireul Jacques, Wissous; Gauthier Rene, Antony, both of France

[73] Assignee: General Electric CGR SA, France

[*] Notice: The portion of the term of this patent subsequent to Jul. 31, 2007 has been disclaimed.

[21] Appl. No.: 860,223

[22] Filed: Mar. 27, 1992

[87] PCT Pub. No.: WO88/00452

PCT Pub. Date: Jan. 28, 1988

Related U.S. Application Data

[63] Continuation of Ser. No. 744,685, Aug. 9, 1991, abandoned, which is a continuation of Ser. No. 314,061, filed as PCT/FR87/00279, Jul. 10, 1987, published as WO88/00452, Jan. 28, 1988, abandoned.

[30] Foreign Application Priority Data

Jul. 18, 1986 [FR] France ................... 86 10476

[51] Int. Cl.⁵ ............................................ A47B 13/00
[52] U.S. Cl. .................................... 5/601; 378/209
[58] Field of Search .................... 5/601, 81.1, 181; 378/208, 209

[56] References Cited

U.S. PATENT DOCUMENTS

| | | | |
|---|---|---|---|
| 1,829,274 | 10/1931 | Gilrag | 5/81.13 |
| 3,588,500 | 6/1971 | Koerner | 269/323 |
| 3,944,204 | 3/1976 | Cesar | 378/209 |
| 4,131,802 | 12/1978 | Braden et al. | |
| 4,567,894 | 2/1986 | Bergman | |
| 4,641,823 | 2/1987 | Bergman | 269/322 |
| 4,727,328 | 2/1988 | Carper et al. | 378/209 X |
| 4,771,785 | 9/1988 | Duer | 269/322 X |
| 4,805,626 | 2/1989 | DiMassimo et al. | 269/322 X |
| 4,944,501 | 7/1990 | Sireul et al. | 269/322 |

FOREIGN PATENT DOCUMENTS

| | | |
|---|---|---|
| 0135161 | 3/1985 | European Pat. Off. |
| 0197827 | 10/1986 | European Pat. Off. |
| 0200374 | 12/1986 | European Pat. Off. |
| 1273267 | 8/1961 | France |
| 1436619 | 3/1966 | France |
| 2151992 | 7/1985 | United Kingdom |

*Primary Examiner*—Michael F. Trettel
*Attorney, Agent, or Firm*—Nilles & Nilles

[57] ABSTRACT

Medical examination table comprised of plate (5), a frame (4) and intermediate means (6) for moving the plate relatively to the frame in order to introduce it into an examination apparatus (1). The means for moving the plate are provided with an elongated moving element (7) of which one end (8) is movable relatively to the frame and the other end (9) is movable relatively to the plate. Said arrangement increases the clearance of the plate with respect to its frame. Moreover, the driving means are disengageable (25) and allow, by operating a knob (30), an emergency withdrawal of the plate from within the examination apparatus, should the patient become indisposed or in the event of a power failure.

32 Claims, 3 Drawing Sheets

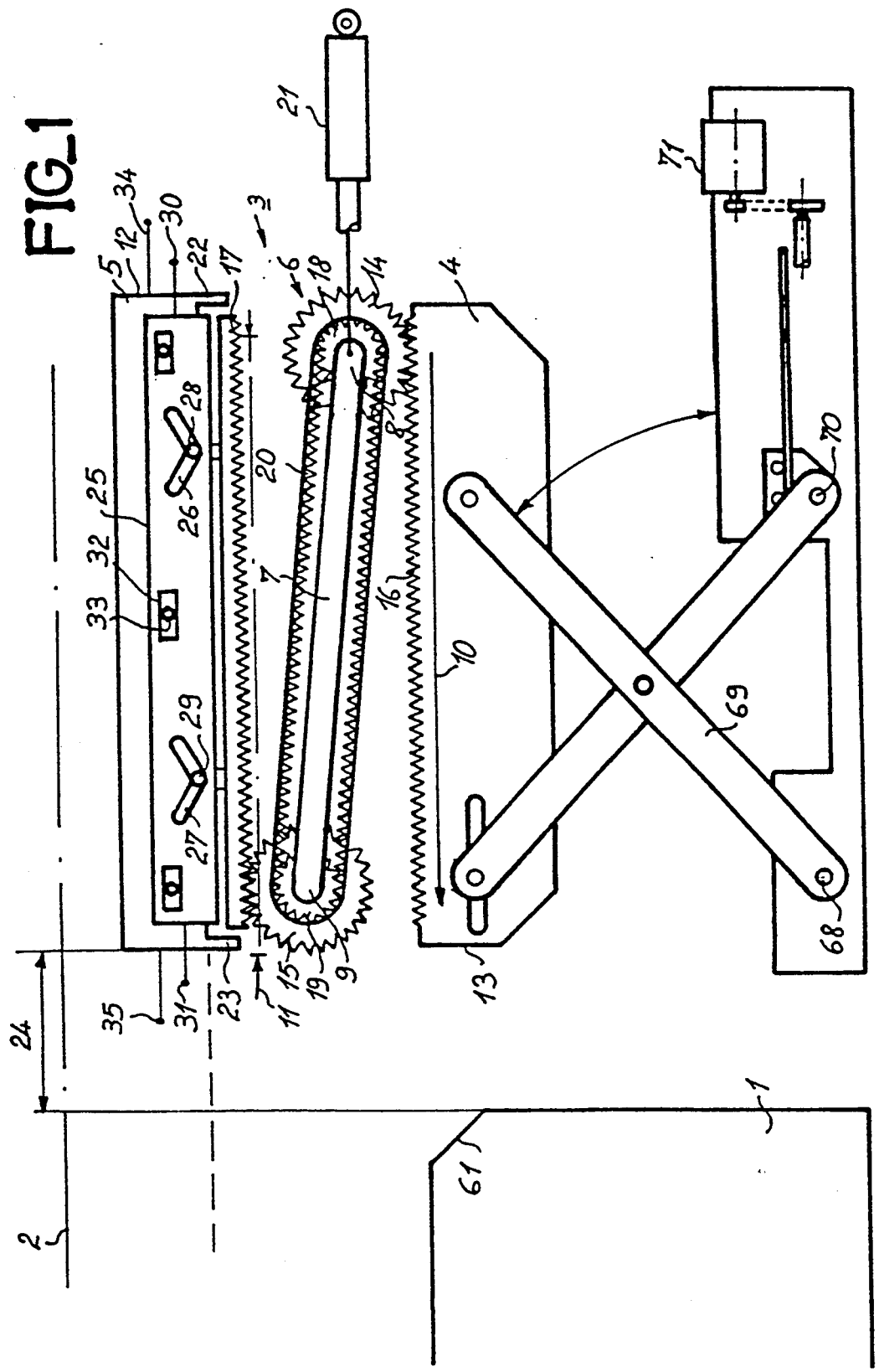

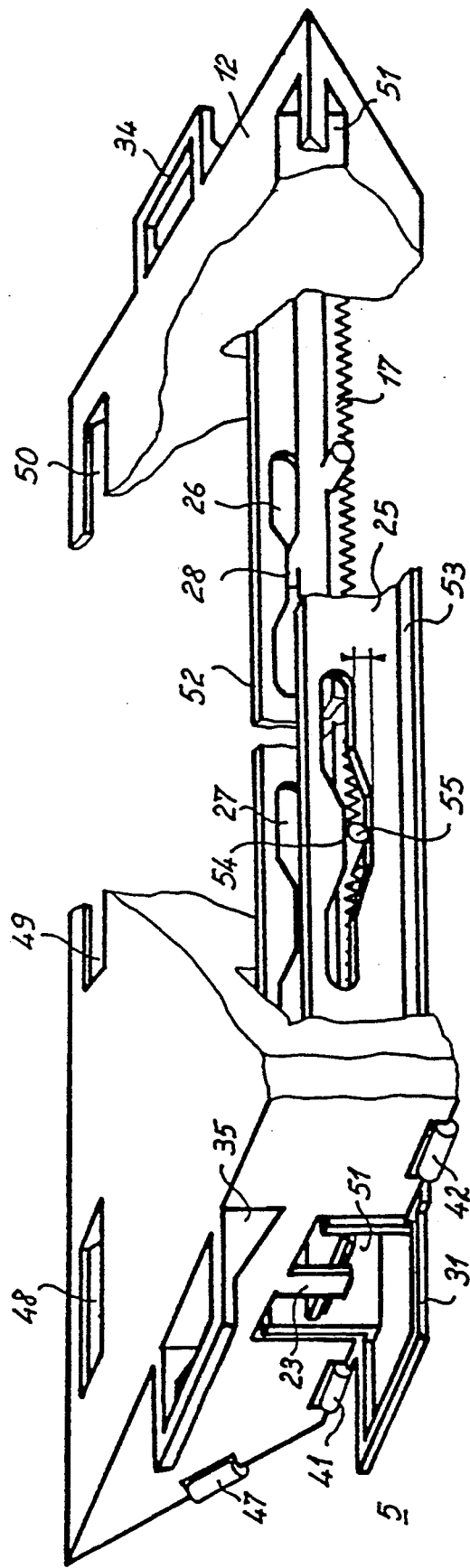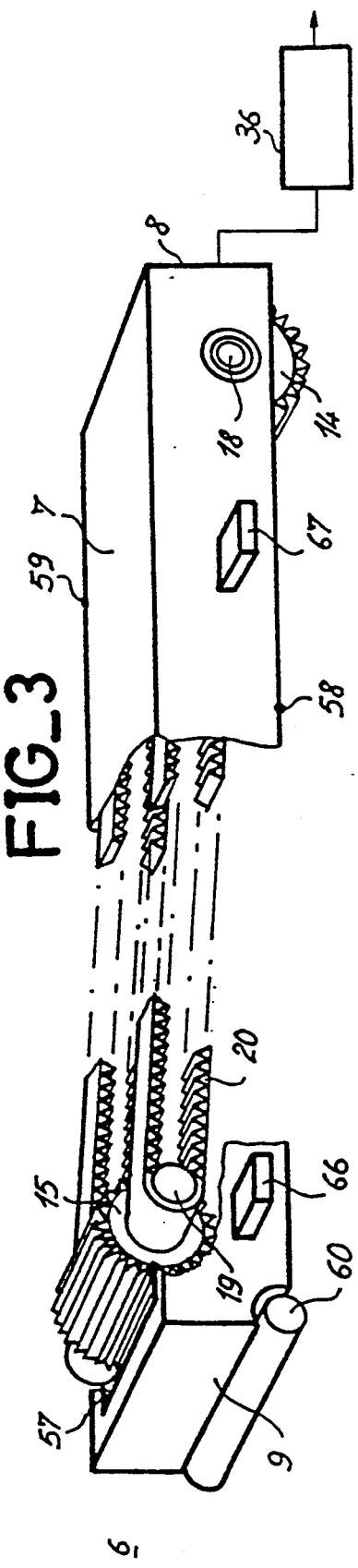

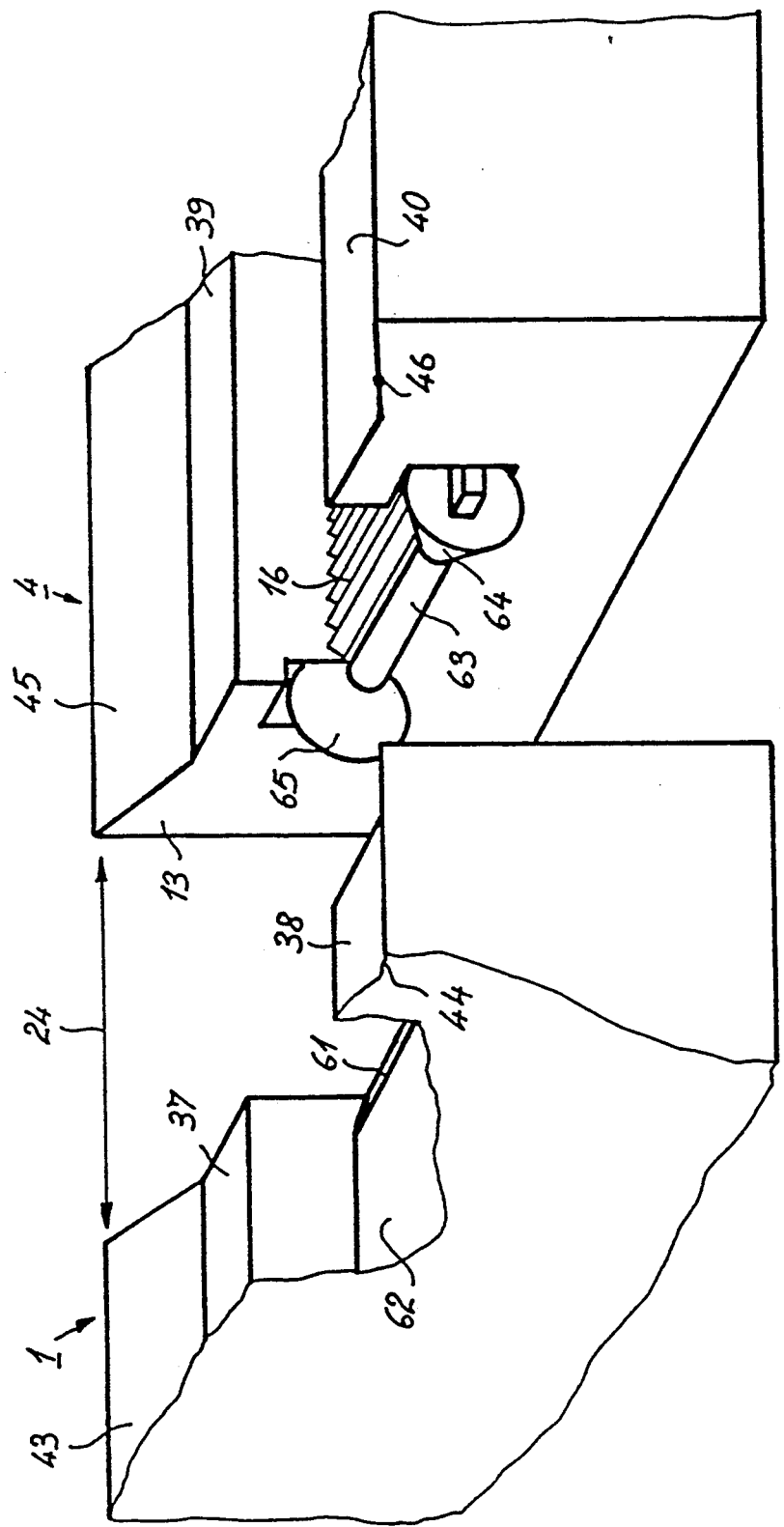
FIG_4

EXAMINATION BED FOR NMR OR TOMODENSITOMETRY APPARATUS

This application is a continuation of application Ser. No. 744,685, filed on Aug. 9, 1991, now abandoned, which is a continuation of Ser. No. 314,061, filed as PCT/FR87/00279, Jul. 10, 1987, published as WO88/00452, filed Jan. 28, 1988, also abandoned.

BACKGROUND OF THE INVENTION

The present invention relates to a medical examination bed notably for use with a nuclear magnetic resonance (NMR) apparatus or a tomodensitometry apparatus. It is mainly used in the medical field where it is known that patients are made to lie down for non-invasive examinations with such machines.

The particularity of this type of examination is that, in general, they take a long time. To improve the comfort of the patient, it may then be necessary to illuminate the machine examination tunnel and to illuminate and talk with the patient. In all cases, it is also necessary to provide constant supervision of the latter. Indeed, patients going through such examinations are generally not in good health and because of this, may be upset by the examination resulting in them not feeling well. Under these conditions, they must be removed from the machine as quickly as possible. Under normal use, the insertion of the patient in the machine, on a plateau or a patient-support panel, is initiated by the starting of motors. These motors may be electrical. In the case of an NMR, it is desirable to have them installed as far as possible from the examination tunnel so as not to interfere with the consistency of the magnetic field, through metallic mass. But the indisposition of the patient may be caused by a power failure. The patient will be aware of the cut-off of lighting, ventilation and of supervision means and will feel some anguish. Intervention to extract the patient from the machine is then rendered difficult because the plateau manipulation motors will have failed because of the lack of current. But because of the mechanical ratios and the demultiplication of these motors, it is unthinkable to attempt to turn the transmission chain backward by hand.

In addition, examination beds may be used for transporting patients into the machine and in some cases bringing them into their bedrooms when the examination is over. Therefore, the beds can be disconnected from the machines. This requirement of bed mobility is incompatible with the nature of the examination being undertaken. Indeed, for such examinations, images and sectional views of parts of the patient's body are taken. These images and sectional views correspond to particular parts of the patient's body. Therefore, it is necessary to identify and move exactly the part of the body to be imaged level with the imagery means. Consequently, when the bed is plugged into the machine, it is essential to bring the means of movement of the patient support panel on the bed to correspond exactly with the means of movement of the panel in the machine. To avoid this difficulty, long panels have been imagined, i.e. 3.50 meters long, still having one end engaged in the bed while the other is entered freely into the apparatus. It can be demonstrated that although already long, this panel may be insufficiently long to permit examination of the whole body. In this case the direction of patient presentation has to be inverted when the need arises. In addition, a long bed is difficult to manipulate through hospital corridors.

SUMMARY OF THE INVENTION

The present invention is designed to remedy the aforementioned drawbacks by proposing beds in which the plateau and means of driving thereof include means to facilitate the manipulation of the patient. On the one hand, the plateau is rendered movable to permit emergency withdrawals. This quality cannot be endowed except to the extent of particularities of plateau guidance on its chassis and through the apparatus with offset setting particularities for the position of the plateau with respect to the apparatus, such particularities being associated with a means of disengaging the plateau from the drive means ensuring its movement. These disengaging means permit exact replacement after emergency action. In addition, the movable character of the plateau makes it possible to reduce the cost of the equipment to be built; it is simply necessary to build a bed chassis and several mobile plateaus placed in turn on the bed chassis in order to be inserted into the machine. This results in the fact that the preparation of patients to be put through examination no longer requires immobilizing the bed and even less so the examination apparatus. On the other hand, the movement of the plateau with respect to the chassis of the bed for its insertion into the apparatus is ensured by using an auxiliary "differential" arm having a length similar to the length of the plateau and/or chassis (2 meters) with one end of such arm driving the plateau while the other rests on the chassis. This is a way of separating the plateau function, supporting the patient proper, from the plateau means of movement function (over a distance greater than the useful length of the latter). The result is that the examination bed according to the invention has a conventional length adapted to its transportation through hospital corridors.

The present invention relates to a medical examination bed, notably for use with an NMR or tomodensitometry apparatus comprising a chassis, an examination plateau and drive means for moving the plateau with respect to its chassis and to an apparatus comprising means for rendering the plateau movable.

BRIEF DESCRIPTION OF FIGURES

The invention will be better understood from the reading of the description which follows and the examination of the accompanying figures. The figures are given for indicative reason and in no way limit the invention. In the figures, the same reference numerals denote the same elements. They show:

FIG. 1: a schematic view of an examination bed according to the invention;

FIG. 2: an exploded perspective view of the movable plateau of the examination bed according to the invention;

FIG. 3: a differential plateau manipulation arm; and

FIG. 4: a perspective view of the guiding path of the plateau on its chassis and in the apparatus.

DETAILED DESCRIPTION OF THE INVENTION

FIG. 1 is a schematic sectional view of an examination bed according to the invention. An NMR apparatus or a tomodensitometer 1 is provided to receive substantially in line with its axis of insertion 2, the patient's body (not shown) supported by an examination bed 3 in accordance with the invention. This examination bed includes a chassis 4, a plateau 5 and drive means 6 for moving the plateau with respect to the chassis and the apparatus. The drive means 6 include a mobile assembly of elongated shape. This mobile assembly includes an arm 7, one end 8 thereof being movable with respect to the chassis and the other end 9 thereof being movable with respect to the 5. Independent of the retention and supporting forces which will be explained subsequently, it can be understood that each point of the plateau 5 can be moved with respect to any point of the chassis by a length equal to the sum of the useful travel 10 of end 8 with respect to the chassis and of the useful travel 11 of end 9 with respect to the plateau. In addition, the arm 7 causes the two end positions of the plateau 5 to be offset with respect to the center of the chassis 4. In the representation of FIG. 1, the plateau is at an end position suitable for preparation for its insertion into the machine. In the other end position, plateau 5 is completely advanced into machine 1 and the rear end 12 of the plateau may be distant from the front end 13 of the chassis by a distance substantially equal to the length of arm 7.

In the example shown, the mobile assembly 6 includes two gear wheels 14 and 15 rotating on shafts integral with the respective ends 8 and 9 of the arm. Gear wheel 14 bears on a rack 16 integral with the chassis while gear 15 bears on a rack 17 connected to the plateau. Pinons, preferably toothed 18 and 19, are respectively rendered integral with the gears 14 and 15. The pinons rotate about an themselves about axis colinear with the wheel shafts. A continuous belt 20, preferably toothed, is tensioned and meshes about the pinons. By means of a motor means, schematically shown by a ram 21, it is possible to push end 8 of arm 7. Rack 16 then causes gear 14 to directly turn driving pinion 18 and to indirectly turn driving pinion 19 through belt 20. Pinion 19 in turn drives the rack 17 of plateau 5 in its movement. The longitudinal movement of rack 17 is limited by two stops 22 and 23 integral with plateau 5.

Consequently, plateau 5 moves with respect to end 9 of the arm by a length related to the movement of end 8 with respect to the chassis 4. The transformation ratio of the movements can be adapted by adjusting the diameters of gears 14 or 15 and/or the diameters of pinions 18 and 19 integral with these gears. In a preferred embodiment, the transformation ratio is 1.

The movement could be obtained by other means. For instance, it would be possible to obtain a mobile assembly 6 with a triple jack, i.e. with at least three interleaved rods. A first rod would have one end attached to the plateau and a third external rod would have one end. That opposite the end of the first rod, attached to the chassis. Under these conditions, it is equivalent to consider the second rod as forming the mobile assembly and having a first end movable with respect to the plateau and a second end movable with respect to the chassis. This solution with hydraulic rams can be replaced by an equivalent screw solution with at least three screws interleaved in one another.

In addition to the end elements, the intermediate elements, the rams or the screws form the mobile assembly. When the intermediate elements are single, the mobile assembly is rigid and non-deformable and corresponds to a rigid bar 7. If the intermediate elements are more numerous, for instance if they include at least interleaved rods, the length of the intermediate element can be variable. In all cases, the invention also offers the advantage of making it possible to approach chassis 4 of the equipment 1 while leaving a gap 24 between these two parts which can be used for any patient preparation operation before the insertion of the patient in a machine. For example, it is possible for an operator to enter the space 24 to arrange the position of the patient's head on the plateau 5, in particular when the head is wearing part of the measurement means needed for the examination to be undertaken, in particular for NMR. Indeed, the examination of the head must be carried out while making sure that the head cannot move during the examination. Therefore, it must be held to prevent it from moving in the image. This retention, which is unpleasant for the patient, must be undertaken at the latest possible stage in order not to frighten the patient. In practice, it is carried out just before entry into machine 1. Without the presence of mobile assembly 6, it would be necessary to insure the fullest possible useful travel of the plateau, to subsequently approach the plateau as close as possible to the machine entry front.

The characteristic of the present invention is the presence in plateau 5 of means of rendering the plateau movable. Schematically, figure depicts plateau 5 retaining a drive rack 17 which meshes with mobile assembly 6 to move the plateau. The rack, maintained in its longitudinal movement by two stops 22 and 23 integral with the plateau, can nevertheless sustain a vertical retraction, disengaging movement, tending to lift it. In this way, the teeth of gear 15 of the mobile assembly escape the notches of rack 17. In one example, the disengaging movement is obtained by means of a plate-cam 25 which maintains in slots, generally V-shaped, such as 26 and 27, supporting shafts, respectively 28 and 29 of rack 17. By simplification, plate 25 is designed to move longitudinally by means of handles 30 or 31 located on either side of the plate 5. It is maintained in its horizontal movement by means which will be described subsequently and serve the same role as the longitudinal windows such as 32 of plate 25, sliding along dowels 33 of plateau 5.

By operating either of the handles, plate 25 is made to move to the right or to the left and drives the shafts 28 and 29 upward. Under this condition, the rack rises and escapes the teeth of gear 15. By working in this way, the means of moving plateau 5 are disengaged. It is then possible to slide the plateau on its supporting means. To facilitate the operation of handle 30 or 31, such handle is matched with another handle, respectively 34 or 35, integral with the plateau, and has a longitudinal offset the value of which is approximately equal to the useful displacement length of plate 25 with respect to the plateau. In practice, taking account of the depth of the teeth in gear 15 and rack 17, and the inclination of the V of the slots 26 or 27 (approximately 30°), it is possible to grasp in one hand both handles 30 and 34 or 31 and 35. By closing the hand, the disengaging of the rack 17 is produced. The force needed to attain this result is low because the rack weight is relatively light. In one example, this effort has been evaluated at a force of approximately 2 kg force. Then, by maintaining the two handles against one another, it is possible to displace plateau 5 in the desired direction in order to extract machine 1.

FIGS. 2 to 4 show a particular example of the construction of plateau 5, moving assembly 6 and chassis 4. As an additional and essential feature, the examination bed according to this invention includes measuring means 36 of the end position 8 of moving assembly 6 with respect to chassis 4. The means 36 may include a tachogenerator or resolvers mounted on gear shaft 18. Since the chassis is designed for placement in a predetermined space 24 of apparatus and since the plateau 5 is, in the normal transportation position of the bed, at a predetermined end position with respect to the chassis, by counting the number of turns effected by the gear 14 or the pinon 18, it is possible to know where any section of the plateau is located in the machine when it is advanced into it. This arrangement offers the advantage of permitting highly tolerant positioning of plateau 5 in the machine. Finally, the conditions of the alignment of plateau 5 with the machine are no longer critical, even for measuring penetration into the machine.

In this way, it is possible to construct a plateau having a V-shape section (FIG. 2), designed to slide on corresponding shaped guides in the apparatus and in the chassis (FIG. 4). The apparatus and the chassis, in a preferred manner, include supporting areas respectively 37-38 and 39-40 designed to receive bearing rollers such as 41-42 (FIG. 2) of plateau 5. In a preferred example, the rollers are of epoxy glass fiber coated with rubber. This provides flexibility for the support and avoids subjecting the patient to disagreeable shaking. To ensure the guidance of the plateau in the machine and the chassis of the bed, those include inclined planes, respectively 43-44 and 45-46 which bear against rollers such as 47 of the plateau 5. In practice, the angle of inclination of the inclined plates is around 30°. This is a compromise between the guidance efficiency to be obtained and the limits at which the rubberized linings come off the glass rollers. In one example, to support the plate, approximately two dozen rollers such as 41-42 are used. For the guide, approximately half a dozen are placed on either side. The plateau can also include side handles such as 48 to 51, regularly distributed on either side of the panel. With these handles, the plateau can be grasped and placed on a gurney for wheeling through the hospital.

In one preferred embodiment, the disengaging device on the rack is slightly different. Rack 17 is flushed-fitted into a groove 51 inside the plateau 5. It is inserted between the two stops including stop 23 which is visible, integral with the plateau. Either side of the rack 17, in groove 51, are entered on edge, two plates 25 and 52 designed to play the same part and ensure symmetry of the lifting force of the rack 17. Handle 31 is designed to longitudinally move the two plates 25 and 52 at the same time. With respect to FIG. 1, the plate guiding device for disengaging the plateau 5 from the rack 17 has been modified. The plates of this embodiment are each provided with a shoe on their lower edge, such as 53 to bear beneath plateau 5 and thus play the same part as dowels 33 in holes 32 of the embodiment of FIG. 1. In a preferred manner, cams 26 and 27 have at the edges and at the center of the V, flat portions forming positions of rests for the lifting force and maintain rack 17. Accordingly, the low and high positions of the rack are mechanically stable. The central flat portion the cams, i.e. flat 54, is designed to apply pressure from top to bottom to the supporting shafts i.e. shaft 55 of the rack to prevent, the lifting of only the relatively light shaft 55 under the drive effect of gear 15. In one example, rather than two sets 26-27 of slots-cams, plates 25 and 52 include approximately ten of them. In this way, there is no need to excessively rigidify rack 17.

The mobile assembly includes arm 7 in which the gears 14 and 15 move at either end. Arm 7 is in the form of a box provided with two openings, for instance opening 57 to permit gears 14 or 15 to protrude beyond the respectively lower surface 58 and upper surface 59 of box 7. The arm also has a front roller 60 to permit its bearing in machine 1 when engaged in it. For this purpose, the input edge of the machine has a chamfer 61 (FIG. 1 and 4) to receive the roller and permit the insertion of the arm into a groove 62, provided in the machine tunnel. In this way, during the greater part of its transfer, the arm rests partly on rack 16 through gear 14 and partly in groove 62 through roller 16. At the exit of chassis 4 there is a connecting block 63 designed to bear under boxed section 7 while head 9 of arm 7 crosses space 24. Tapered ends or cones 64 and 65 of connecting block 63 compensate for alignment faults between the machine. It is intended to provide the side edges of arm 7 with blocks such as 66 or 67, preferably of polytetrafluoroethylene to bear on the vertical sides of the grooves in chassis 4 and of machine 1. The overall height of the arm is calculated so that the arm can be housed within grooves 51 and 61 or between racks 16 and 17, without applying any supporting force to the plateau.

The bed and/or chassis according to the invention can also be provided with the aforementioned attached devices.

In addition, and by preference, the bed 3 is adjustable for height in order to suit all different machines and to facilitate the loading of any non bedridden patient enabling him to sit on the plateau near the ground. The elevation of the bed is caused by the rotation of the legs through an angle X. In a preferred embodiment, base 68 of one of the legs, leg 69 is held fixed with respect to machine 1 while the base of the other leg can slide toward base 68 under the effect of motor 71. Under these conditions, the gap 24 between the bed and the machine varies as a function of the bed's height in order to facilitate, even more in the low position, passage of the operator during the rising movement. The bed is put through a rotation movement to reduce the gap separating it from the machine.

We claim:

1. A medical examination unit comprising:
an examination means for examining a patient; and
a medical examination bed;
said medical examination bed including
a chassis,
a movable plateau which is movable with respect to said chassis,
drive means or moving said plateau in a predetermined direction with respect to said chassis and with respect to said examination means for permitting the insertion of said plateau into said examination means and the withdrawal of said plateau from said examination means,
first rack means, extending along a length of said plateau, for enabling said plateau to move in said predetermined direction, and
means for disengaging said plateau drive means, said disengaging means comprising retracting means in said plateau for supporting said first rack means and for moving said first rack means in a direction away from said drive means without raising said plateau,
wherein said examination means is aligned with said bed, and said chassis and examination means include support means for receiving and guiding said plateau,
wherein said plateau drive means include a mobile assembly having first and second ends, the moving of said mobile assembly being translational with respect to said plateau and said chassis, said mobile assembly having an elongated shape, wherein the first end of said mobile assembly is mechanically connected to said chassis and is movable by translation with respect to said chassis, and the second end of said mobile assembly is mechanically connected to the plateau and is movable by translation with respect to said plateau.

2. A medical examination unit according to claim 1, wherein said retracting means include means for moving said first rack means at right angles to the direction of movement of the plateau.

3. A medical examination unit according to any of claims 1, wherein the plateau defines a trapezoid-shaped profile for resting by gravitation, independent of the plateau drive means and approximately at the center of said direction of movement of said plateau.

4. A medical examination unit according to any of claims 1, wherein said plateau includes means for providing a gap between the examination means and the plateau.

5. A medical examination unit according to claim 1, wherein the retracting means include at least one plate provided with cams whereby the first rack means is moved when said plate is operated; and at least one set of handles attached to the plate and the plateau to guide said movement.

6. A medical examination unit according to claim 1, wherein said mobile assembly includes an arm having mobile drive means at one end for moving the arm respectively in translation with respect to the chassis and the plateau with respect to the arm.

7. A medical examination unit according to claim 6, wherein the arm includes two drive gears, one of said drive gears meshing with said first rack means and the other drive gear meshing with a second rack means connected to the chassis.

8. A medical examination unit according to claim 7, wherein said plateau drive means include a belt having teeth which mesh with the drive gears.

9. A medical examination unit according to claim 6, wherein the arm includes a roller in an area near the examination means to permit the insertion of the arm into the examination means.

10. A medical examination unit according to claim 6, wherein the examination means and the chassis include grooves to receive the arm, and the arm is provided with side blocks to ensure the guidance of the arm between the sides of the grooves.

11. A medical examination unit according to claim 6, wherein the plateau and the arm are made of non-magnetic and non-metallic materials.

12. A medical examination unit according to claim 1, wherein said mobile assembly comprises means for making movements of said mobile assembly with respect to its ends mechanically dependent.

13. A medical examination unit according to claim 12, wherein a ratio of the movements between the first end of the mobile assembly and the chassis and the second end of the mobile assembly and the plateau is one.

14. A medical examination unit according to claim 1, wherein the chassis includes, at one end near the examination means, alignment means comprising, two opposed cones for aligning said chassis and said plateau with said examination means.

15. A medical examination unit according to claim 1, wherein said mobile assembly includes means for measuring a position of the plateau with respect to the examination means by measuring a position of the end of the mobile assembly connected to the chassis.

16. A medical examination unit according to claim 1, wherein said examination means is an NMR apparatus.

17. A medical examination unit according to claim 1, wherein said examination means is a tomodensitometry apparatus.

18. A medical examination bed for use with an NMR or tomodensitometry apparatus comprising:
   a chassis;
   a movable plateau which is movable with respect to said chassis;
   drive means or moving said plateau in a predetermined direction with respect to said chassis and with respect to said apparatus;
   first rack means, extending along a length of said plateau for enabling said plateau to move in said predetermined direction; and
   means for disengaging said plateau drive means, said disengaging means comprising retracting means in said plateau for supporting said first rack means and for moving said first rack means in a direction away from said drive means without raising said plateau,
wherein:
   said apparatus is aligned with said bed, and said chassis and apparatus include support means for receiving and guiding said plateau; and
   said plateau drive means include a mobile assembly having first and second ends, the movement of said mobile assembly being translational with respect to said plateau and said chassis, said mobile assembly having an elongated shape, wherein the first end of said mobile assembly is mechanically connected to said chassis and is movable by translation with respect to said chassis, and the second end of said mobile assembly is mechanically connected to the plateau and is movable by translation with respect to said plateau.

19. A bed according to claim 18, wherein said retracting means include means for moving said first rack means at right angles to the direction of movement of the plateau.

20. A bed according to any of claims 18 or 19, wherein the plateau defines a trapezoid-shaped profile for resting by gravitation, independent of the plateau drive means and approximately at the center of said direction of movement of said plateau.

21. A bed according to any of claims 18 or 19, wherein said plateau includes means for providing a gap between the apparatus and the plateau.

22. A bed according to claim 18, wherein the retracting means include at least one plate provided with cams whereby the first rack means is moved when said plate is operated; and at least one set of handles attached to the plate and the plateau to guide said movements.

23. A bed according to claim 18, wherein said mobile assembly includes an arm having mobile drive means at one end for moving the arm respectively in translation with respect to the chassis and the plateau with respect to the arm.

24. A bed according to claim 23, wherein the arm includes two drive gears, one of said drive gears meshing with said first rack means and the other drive gear meshing with a second rack means connected to the chassis.

25. A bed according to claim 24, wherein said plateau drive means include a belt having teeth which mesh with the drive gears.

26. A bed according to claim 23, wherein the arm includes a roller in an area near the apparatus to permit the insertion of the arm into the apparatus.

27. A bed according to claim 23, wherein the apparatus and the chassis include grooves to receive the arm, and the arm is provided with side blocks to ensure the guidance of the arm between the sides of the grooves.

28. A bed according to claim 23, wherein the plateau and the arm are made up of non-magnetic and non-metallic materials.

29. A bed according to claim 18, wherein said mobile assembly comprises means for making movements of said mobile assembly with respect to its ends mechanically dependent.

30. A bed according to claim 29, wherein a ratio of the movements between the first end of the mobile assembly and the chassis and the second end of the mobile assembly and the plateau is one.

31. A bed according to claim 18, wherein the chassis includes, at one end near the apparatus, alignment means comprising, two opposed cones for aligning said chassis and said plateau with said apparatus.

32. A bed according to claim 18, wherein said mobile assembly includes means for measuring a position of the plateau with respect to the apparatus by measuring a position of the end of the mobile assembly connected to the chassis.

* * * * *